(12) United States Patent
Neeves et al.

(10) Patent No.: US 9,709,579 B2
(45) Date of Patent: Jul. 18, 2017

(54) MICROFLUIDIC FLOW ASSAY AND METHODS OF USE

(71) Applicant: Colorado School of Mines, Golden, CO (US)

(72) Inventors: Keith B. Neeves, Denver, CO (US); Abimbola Onasoga, Golden, CO (US)

(73) Assignee: Colorado School of Mines, Golden, CO (US)

( * ) Notice: Subject to any disclaimer, the term of this patent is extended or adjusted under 35 U.S.C. 154(b) by 0 days.

(21) Appl. No.: 13/929,141

(22) Filed: Jun. 27, 2013

(65) Prior Publication Data

US 2014/0038214 A1 Feb. 6, 2014

Related U.S. Application Data

(60) Provisional application No. 61/665,177, filed on Jun. 27, 2012.

(51) Int. Cl.
   *C12Q 1/56* (2006.01)
   *G01N 33/86* (2006.01)

(52) U.S. Cl.
   CPC .................................. *G01N 33/86* (2013.01)

(58) Field of Classification Search
   None
   See application file for complete search history.

(56) References Cited

U.S. PATENT DOCUMENTS

| | | | |
|---|---|---|---|
| 5,561,070 A * | 10/1996 | Stewart et al. | 436/526 |
| 7,318,902 B2 | 1/2008 | Oakey et al. | |
| 2001/0046453 A1* | 11/2001 | Weigl et al. | 422/102 |
| 2002/0103352 A1* | 8/2002 | Sudor | 536/23.1 |
| 2004/0005582 A1* | 1/2004 | Shipwash | G01N 33/54366 435/6.19 |
| 2004/0147032 A1* | 7/2004 | Martin | B01L 3/5027 436/69 |
| 2011/0039285 A1* | 2/2011 | Sadaba Champetier De Ribes et al. | 435/13 |
| 2013/0121918 A1* | 5/2013 | Hong et al. | 424/9.1 |

OTHER PUBLICATIONS

Maloney (Publicly accessible Penn Dissertations, Paper 167 (2010).*
Ishihara et al (J. R. Soc. Interface., 6:S279-291 (2009).*
Simonnet et al (App. Phys. Let. 87:114104-1-10 (2005).*
Chandler, Am. J. Clin. Pathol.,134:90-96 (2010).*
Colace et al., Bioconjug Chem., 22(10): 2104-2109 (2011).*
Neeves et al., J. Thromb. Haemost., 6:2193-2201 (2008).*
Neuenschwander et al., JBC, 268(29) 21489-21492 (1993).*
Shen et al., Arterioscler. Thromb. Vasc. Biol., 28:2035-2041 (2008).*
Sundararajan et al., J. Microelectromech. Sys. 13(4):559-567 (2004).*
Buranda et al., Langmuir, 19:1654-1663 (2003).*
Zhang et al., Microelectronic Eng. 78-79:556-562 (2005).*
Wang et al., Electrochem. Comm., 12:258-261 (2010).*
Cho et al., Nano Lett., 8(12):4386-4390 (2008).*
Tennico et al., Anal. Chem., 82:5591-5597 (2010).*
Xiao et al., Angew. Chem., 117:5592-5595 (2008).*
Wei et al., Chem. Commun., 3735-3737 (2007).*
Runyon et al (JACS, 103:3458-3464 (2008).*
Forouzana et al., Lab Chip, 11:1924-1932 (2011).*
Du et al., Lab Chip, 9(6):741-848 (2009).*
Duffy et al. "Rapid Prototyping of Microfluidic Systems in Poly(dimethylsiloxane)" Analytical Chemistry, Dec. 1998, vol. 70, No. 23, pp. 4974-4984.
Gemmell et al. "Flow as a Regulator of the Activation of Factor X by Tissue Factor," Blood, Oct. 1988, vol. 72, No. 4, pp. 1404-1406.
Kastrup et al. "Modular chemical mechanism predicts spatiotemporal dynamics of initiation in the complex network of hemostasis," Proceedings of the National Academy of Sciences, Oct. 2006, vol. 103, No. 43, pp. 15747-15752.
Kastrup et al. "Characterization of the Threshold Response of Initiation of Blood Clotting to Stimulus Patch Size," Biophysical Journal, Oct. 2007, vol. 93, No. 8, pp. 2969-2977.
Repke et al. "Hemophilia as a defect of the tissue factor pathway of blood coagulation: Effect of factors VIII and IX on factor X activation in a continuous-flow reactor," Proceedings of the National Academy of Sciences, Oct. 1990, vol. 87, pp. 7623-7627.
Runyon et al. "Propagation of Blood Clotting in the Complex Biochemical Network of Hemostasis Is Described by a Simple Mechanism," Journal of the American Chemical Society, Jun. 2007, vol. 129, No. 22, pp. 7014-7015.
Runyon et al. "Effects of Shear Rate on Propagation of Blood Clotting Determined Using Microfluidics and Numerical Simulations," Journal of the American Chemical Society, Mar. 2008, vol. 130, No. 11, pp. 3458-3464, supporting information pp. S1-S9.
Shen et al. "Threshold Response of Initiation of Blood Coagulation by Tissue Factor in Patterned Microfluidic Capillaries Is Controlled by Shear Rate," Arteriosclerosis, Thrombosis, and Vascular Biology, Nov. 2008, vol. 28, No. 11, pp. 2035-2041, supplemental information 10 pages.
Shen et al. "Confinement Regulates Complex Biochemical Networks: Initiation of Blood Clotting by "Diffusion Acting"," Biophysical Journal, Oct. 2009, vol. 97, No. 8, pp. 2137-2145.
Neeves et al. "Throbin Flux and Wall Shear Rate Regulate Fibrin Fiber Deposition State during Polymerization under Flow," Biophysical Journal, Apr. 2010, vol. 98, pp. 1344-1352.

\* cited by examiner

*Primary Examiner* — Thomas J Visone
(74) *Attorney, Agent, or Firm* — Sheridan Ross P.C.

(57) ABSTRACT

A microfluidic-based flow assay and methods of manufacturing the same are provided. Specifically, the microfluidic flow assay includes a substrate surface comprising lipid coated particles and microfluidic channels through which a blood product can flow. The lipid coated particles comprise functional molecules that can induce or inhibit the coagulation cascade.

23 Claims, 16 Drawing Sheets

MICROFLUIDIC FLOW ASSAY AND METHODS OF USE

CROSS-REFERENCE TO RELATED APPLICATIONS

This application claims the benefit of U.S. Provisional Patent Application Ser. No. 61/665,177, filed Jun. 27, 2012, the entire disclosure of which is hereby incorporated herein by reference.

TECHNICAL FIELD

The invention relates to a microfluidic-based flow assay and device for use in analyzing bleeding and anticoagulation disorders, dosing anticoagulant drugs, tracking the effects of pharmacological interventions on coagulation, and methods of making the same.

BACKGROUND OF INVENTION

Maintaining the balance between bleeding and thrombosis remains one of the greatest challenges facing the biomedical community. Excessive bleeding is an important medical issue. For example, post partum bleeding represents a leading cause of maternal mortality and causes serious morbidity in developing countries. Individuals with genetic bleeding disorders, such as hemophilia, have a decreased ability to clot blood because of deficiencies in certain coagulation factors.

On the other end of the spectrum, excessive clotting, or thrombosis, is a major complication of surgery and is integrally involved in atherosclerosis, obesity, infection, diabetes, cancer, and autoimmune disorders. Over the last decade, significant advances have been made in understanding the molecular basis of bleeding and thrombotic disorders; however, a large portion of the observed variability remains unknown.

Parallel with these discoveries, there has been a rapid development of new drugs such as recombinant proteins for replacement and interventional therapies. Interestingly, what remains strikingly deficient in clinical hematology are techniques to diagnose a very broad range of disorders of both deficient and excessive clotting as well as to monitor the effects of therapeutic interventions.

The formation of a stable fibrin network is necessary for hemostasis, which requires fibrinogen conversion to fibrin. In purified systems containing only thrombin and fibrinogen, it has been shown that fibrin polymerization can only occur in a narrow set of conditions that are defined by the rate of thrombin formation and the shear rate (Neeves et al., Biophysical Journal, 2010, 98; 1344-1352). Most coagulation assays do not account for the interplay between flow and surface reactions, which could affect clot properties like fiber thickness, fibrin clot height, fiber alignment with flow, and resistance to lysis. These properties can be useful in differentiating plasma clots of healthy individuals from those with thrombotic or haemostatic disorders.

Diagnosing the severity of bleeding a disorder is impossible with current bleeding assays, particularly because most current bleeding assays test for either platelet function and/or platelet coagulation using whole blood, however, these assays do not allow for the use plasma. Additionally, most existing solutions do not properly create an environment which properly simulates a natural human wound or point of bleeding. Also, most of these conventional assays occur under static, or no flow, conditions. Since blood is a moving fluid, however, there are several advantages to studying it under flow in bleeding diagnostics.

SUMMARY OF INVENTION

One embodiment of the invention relates to a microfluidic device comprising at least one microfluidic channel and at least one substrate surface in the microfluidic channel. The substrate surface comprises a plurality of lipid coated particle that are immobilized on the substrate surface. The lipid coated particles comprise at least one functional molecule that induces coagulation.

In one aspect, the substrate surface is functionalized glass.

In another aspect, the plurality of lipid coated particles comprises a plurality of particles having a hydrophilic surface. In one aspect, the lipid coated particles comprise one or more phospholipid structures. The phospholipid structures can be selected from phosphotidylserine, phosphotidlcholine, phosphatidic acid, phosphatidylethanolamine, phophoinositides, phosphosphingolipids, and combinations thereof. In still another aspect, the plurality of lipid coated particles is immobilized to the substrate surface by an immobilization method. The immobilization can be selected from covalent bonding, electrostatic interactions and hydrogen bonding. In yet another aspect, the immobilized plurality of lipid coated particles is patterned to the substrate surface by a patterning method. The patterning method can be selected from microblotting and microstenciling. In another aspect, the immobilized and patterned lipid coated particles are integrated into at least one microfluidic channel.

In another aspect, the microfluidic device further comprises hydrodynamic focusing.

In still another aspect, the functional molecule of the coated lipid particle of the device is one or more transmembrane proteins. The transmembrane proteins can be selected from tissue factor, thromobomodulin, endothelial cell protein C receptor, glycoprotein IIb/IIIa, glycoprotein VI, glycoprotein Ib/IX/V, P-selectin, glycoprotein IV, CD9, platelet endothelial cell adhesion molecule (PECAM-1), Ras-related protein 1b (rap1b), c-type lectin-like receptor 2 (CLEC-2), intracellular adhesion molecule 1 (ICAM-1), intracellular adhesion molecule 2 (ICAM-2) and combinations thereof.

Another embodiment of the invention relates to a microfluidic device made by a method comprising providing a substrate, creating at least one surface on the substrate, immobilizing and patterning a plurality of lipid coated particles onto the surface of the substrate. The lipid coated particles are coated with lipid bilayers and comprise a functional molecule that induces coagulation. The plurality of lipid coated molecules is integrated into at least one microfluidic channel, which intersects at least a portion of the substrate surface.

Another embodiment of the invention relates to a plurality of lipid coated particles made by a method comprising providing silica beads, making the silica beads hydrophilic, coating the surface of the hydrophilic silica beads with lipid bilayers and a functional molecule. The lipid bilayers comprise one or more phospholipid structures.

Yet another embodiment of the invention relates to a kit for measuring clotting characteristics of a blood product. The kit comprises a hermetically sealed microfluidic device, the microfluidic device comprising at least one microfluidic channel and at least one substrate surface provided in the at least one microfluidic channel, wherein the at least one substrate surface comprises a lipid coated particle wherein the lipid coated particle comprises a functional molecule embedded in the lipid, wherein the functional molecule induces coagulation.

A further embodiment of the invention relates to a method for evaluating a blood product of an individual comprising perfusing the individual's blood product over a microfluidic device under flow conditions to contact the blood product with a functional molecule of a plurality of coated lipid particles, wherein the microfluidic device, comprises at least one microfluidic channel; and at least one substrate surface provided in the at least one microfluidic channel, wherein the at least one substrate surface comprises a plurality of lipid coated particles immobilized on the substrate surface, wherein the plurality of lipid coated particles comprises at least one functional molecule, wherein the at least one functional molecule induces coagulation; and detecting one or more coagulation products associated with the at least one functional molecule of the plurality of the lipid coated particles. In one aspect, the blood product is selected from whole blood, plasma, platelet rich plasma, and platelet poor plasma. In another aspect, the flow conditions simulate hemodynamic conditions of the individual. In still another aspect of the method, the functional molecule is one or more transmembrane proteins. The transmembrane proteins can be selected from tissue factor, thromobomodulin, endothelial cell protein C receptor, glycoprotein IIb/IIIa, glycoprotein VI, glycoprotein Ib/IX/V, P-selectin, glycoprotein IV, CD9, platelet endothelial cell adhesion molecule (PECAM-1), Ras-related protein 1b (rap1b), c-type lectin-like receptor 2 (CLEC-2), intracellular adhesion molecule 1 (ICAM-1), intracellular adhesion molecule 2 (ICAM-2) and combinations thereof. In yet another aspect, the functional molecule initiates coagulation. In still another aspect, the functional molecule inhibits coagulation.

In yet another aspect of the method, the step of detecting comprises quantifying the coagulation product. The coagulation product can be selected from thrombin, fibrin, thrombin-antithrombin complex, fibrinopeptide A, fibrinopeptide B, D-dimer, prothrombin fragment 1+2, activated factor X, activated factor V, activated factor VIIIa, activated factor IXa, activated factor XIa, activated factor XIIa, activated protein C, activated protein S, and mixtures thereof. In still another aspect of the method, the coagulation product can be detected by a method selected from brightfield microscopy, darkfield microscopy, fluorescence microscopy, multi-photon excitation, second harmonic generation, third harmonic generation, atomic force microscopy, scanning electron microscopy, and absorbance.

BRIEF DESCRIPTION OF DRAWINGS

FIG. 9A' shows thrombin generation for factor deficient plasma at 50 $s^{-1}$ and TF concentration of 50 molecules/$\mu m^2$ using the assay described in FIGS. 6D-6F. Normal pooled plasma (NPP); plasma deficient with factor XI (FXI-def); plasma deficient with factor VIII (FVIII-def); and plasma deficient with factor IX (FIX-def).

FIG. 9B' shows thrombin generation for factor deficient plasma at 5 $s^{-1}$ and TF concentration of 5 molecules/$\mu m^2$ using the assay described in FIGS. 6D-6F. Normal pooled plasma (NPP); plasma deficient with factor XI (FXI-def); plasma deficient with factor VIII (FVIII-def); and plasma deficient with factor IX (FIX-def).

DETAILED DESCRIPTION

This invention generally relates to a microfluidic device and methods and uses of the device for evaluating and testing a blood product from an individual as well as for measuring the clotting characteristics of a blood product from an individual. This invention describes a flow based assay that allows the use of a blood product such as plasma for measuring end products of the coagulation cascade (such as thrombin and fibrin generation). The advantage of this invention is that it integrates the coagulation cascade into a fluidic architecture, which allows for measurement of coagulation products under the hemodynamic conditions found in the body. Furthermore, because this assay allows the use of plasma, the plasma samples can be stored for long periods of time before being tested. This is in contrast to most flow based assays that use only whole blood, which needs to be used within hours of a blood draw.

This invention fills a technology gap for a flow based plasma assay for measuring coagulation potential.

There are no known flow based plasma assays for coagulation. Static plasma assays for measuring coagulation include thrombin generation (TG), prothrombin time (PT), partial thromboplastin time (PTT), and turbidity-based assays.

Figure 1:
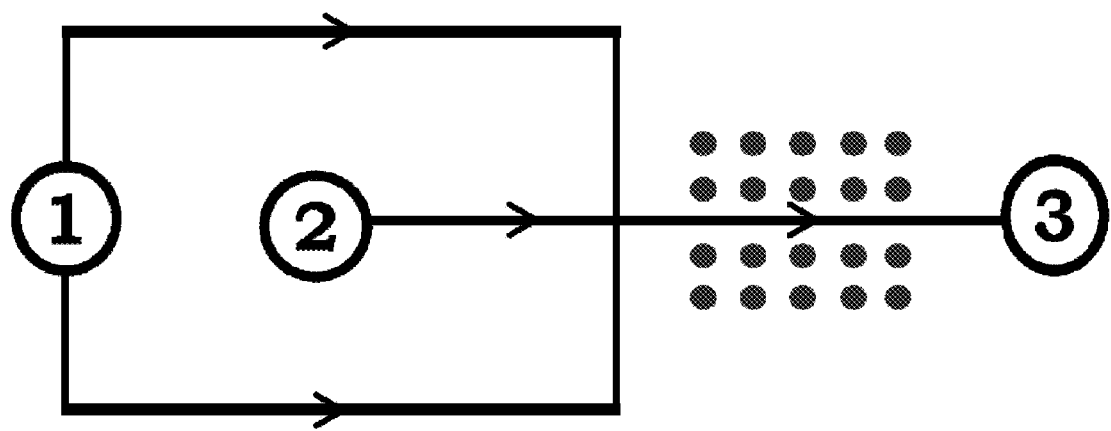
FIG. 1 depicts a top view of an exemplary microfluidic device with at least some embodiments of the present invention.

With reference to FIG. 1 an embodiment of the present invention is illustrated. This is an exemplary microfluidic device in accordance with at least some embodiments of the present invention. More specifically, the microfluidic device may include one or more fluid receiving passages which allows for fluid to flow through a microfluidic device; an inlet for a blood product (such as plasma) which is capable of receiving a blood product (shown as "2") and an outlet (shown as "3") where blood product can be collected. The microfluidic device may also include a buffer inlet for hydrodynamic focusing (shown as "1") which is capable of receiving buffer. Each shaded circular spot represents a plurality of lipid coated particles of the invention that is attached to a substrate surface. The arrows represent the direction of flow of the blood product and buffer through the channels of the microfluidic device.

Figure 2:
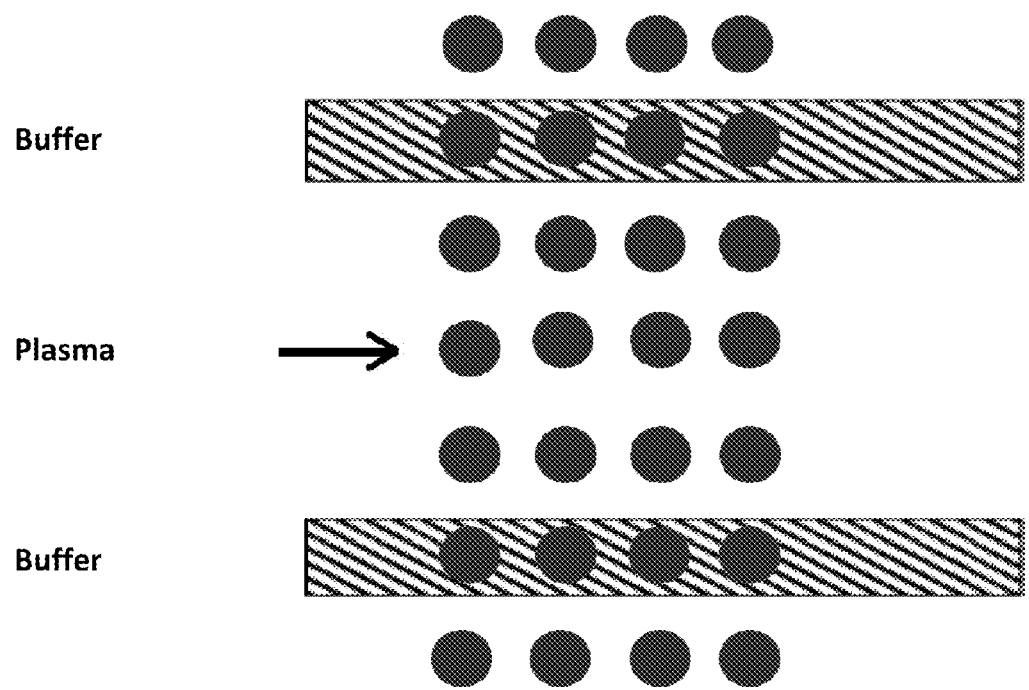
FIG. 2 depicts an exploded top view of a portion of an exemplary microfluidic device with at least some embodiments of the present invention.

With reference to FIG. 2 an embodiment of the present invention is illustrated. This is an exploded top view of an exemplary microfluidic device as described in FIG. 1 with at least some embodiments of the present invention. Each shaded circular spot represents a plurality of lipid coated particles of the invention that plasma flows over. The buffer sections represent buffer that is flowed adjacent to the plasma over the spots demonstrating focusing of the plasma on the spots.

Figure 3:
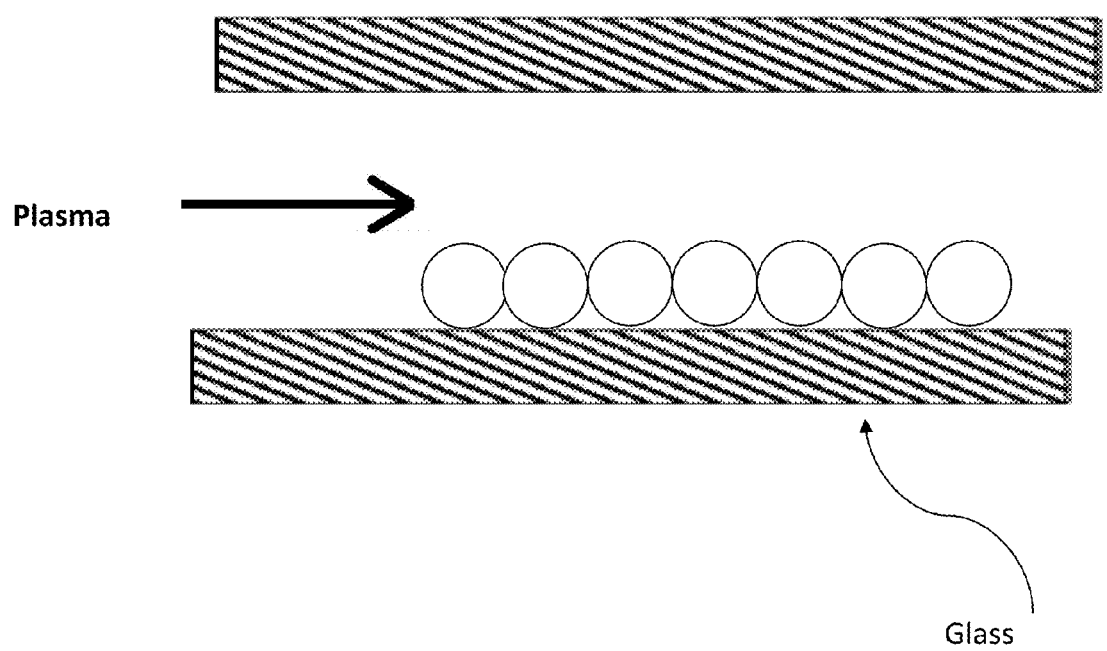
FIG. 3 depicts an exploded side-view of a portion of an exemplary microfluidic device with at least some embodiments of the present invention.

With reference to FIG. 3 an embodiment of the present invention is illustrated. This is an exploded side-view of a portion of an exemplary microfluidic device as described in FIG. 1 with at least some embodiments of the present invention. Each circle represents an individual single lipid coated particle within a single circular spot as depicted in FIGS. 1 and 2.

The device of the present invention comprises at least one microfluidic channel. The microfluidic device may include a plurality of fluid-filled receiving passages, which are capable of receiving fluid at a receiving end and allowing the fluid to flow through a microfluidic channel to a collection point or terminal end. One or more microfluidic channels may be present and may spilt into multiple channels, thereby resulting in a number of terminal ends. The number of receiving ends may equal the number of terminal ends. The configuration and design of the microfluidic channels can vary without departing from the scope of the present invention.

In addition to comprising at least one microfluidic channel, the microfluidic device may also comprise at least one substrate surface which intersects one or more of the microfluidic channels. In addition, the substrate surface can be functionalized. In this step, the substrate surface may be treated with 3-aminopropyl-trimethoxysilane (APTMS), thereby creating a monolayer of APTMS on the upper surface of the substrate. Methods of rendering substrates, such as glass substrates, hydrophilic are well known in the art. Method of functionalizing the substrate include, without limitation, rendering the substrate and/or the substrate surface hydrophilic, hydrophobic, reactive (via amine or carboxylic acid groups) or some other chemistry. In one embodiment, silane chemistries may be used on the substrates. The substrate may be any composed of any material including but not limited to glass, plastic, gold, quartz, silicon, silicon nitride, silicon dioxide, polydimethylsiloxane, polystyrene, polymethyl methacrylate and combinations thereof, or any other type of known substrate material used in surface chemistry. Additionally, the substrate is a size that allows for complete immersion of the substrate and/or substrate surface into the microfluidic channel.

The substrate surface comprises a plurality of lipid coated particles that are immobilized on the substrate surface. The lipid coated particles may be comprised of silica such as silica glass or ceramics, including but not limited to silica beads that are synthesized by methods known to those of skill in the art, including but not limited to the Stöber process. The resulting silica beads may be silica micro beads and may range in diameter from about 0.1 micrometer to about 100 micrometers. Preferably, the resulting silica beads are 1 to 10 micrometers in diameter.

In the case of lipid coated particles formed using silica beads, once the silica beads are synthesized they may be made hydrophilic by using known methods including but not limited to treatment with hydrogen peroxide and dilute organic acid. Once the beads are synthesized and made hydrophilic, their surfaces may be coated with lipid bilayers comprised of one or more phospholipid structures. These phospholipid structures include but are not limited to phosphatidylserine, phosphatidylcholine, phosphatidic acid, phosphatidylethanolamine, phophoinositides, phosphosphingolipids, and combinations thereof. The composition of the lipid bilayer may be altered to mimic the surface of various cell types, such as platelets, leukocytes, erythrocytes, endothelial cells or smooth muscle cells. This alteration may be accomplished by mixing different ratios of the phospholipid structures, such as phosphatidylserine and phosphatidylcholine and phosphatidylethanolamine. Other combinations of two or more of the phospholipid structures may also be mixed.

The lipid coated particles in addition to being coated with lipid bilayers, also are comprised of one or more functional molecules which are contained within the lipid bilayers. The functional molecule may be any transmembrane protein. Such transmembrane protein may include transmembrane proteins that are known to regulate blood coagulation including but not limited to tissue factor, thromobomodulin, endothelial cell protein C receptor and combinations thereof. Thrombin is a known serine protease that creates a biopolymer of fibrin by cleaving fibrinopeptide from the plasma protein of fibrinogen. Fibrin forms a highly entangled hydrogel that provides the scaffold onto which a blood clot grows. Generally, high concentrations of thrombin are created during the extrinsic or tissue factor pathway of the coagulation cascade, hence why tissue factor is known as a coagulation cascade inducing agent. Other transmembrane proteins may include proteins that are known to be receptors for cell to cell adhesion including but not limited to glycoprotein IIb/IIIa, glycoprotein VI, glycoprotein Ib/IX/V, P-selectin, glycoprotein IV, CD9, platelet endothelial cell adhesion molecule (PECAM-1), Ras-related protein 1b (rap1b), c-type lectin-like receptor 2 (CLEC-2), intracellular adhesion molecule 1 (ICAM-1), intracellular adhesion molecule 2 (ICAM-2) and combinations thereof. The lipid coated particles may contain various concentrations of one or more of the functional molecules.

Once the lipid coated particles are synthesized and coated as discussed above, they are immobilized to the substrate surface. Methods to immobilize silica beads, such as the lipid coated particles of the present invention, are known to those of skill in the art and include but are not limited to covalent bonding, electrostatic interactions and hydrogen bonding. The immobilization method provides an adequate attractive force between the lipid coated particles and the substrate surface to withstand shear stresses during the assay.

Figure 4:
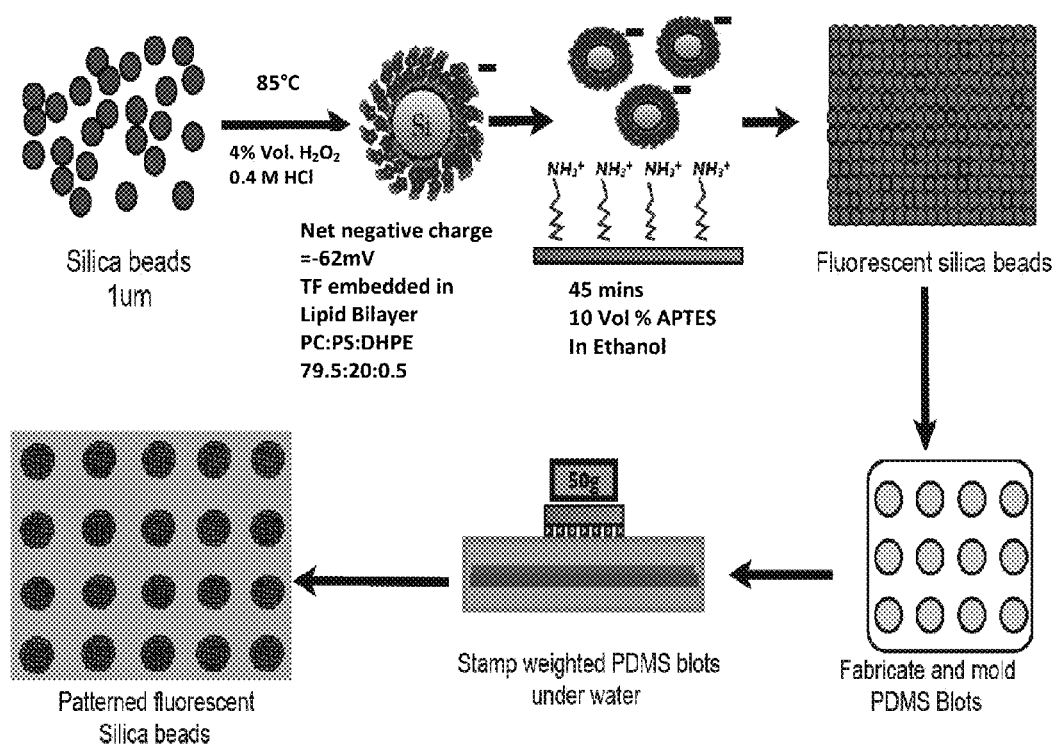
FIG. 4 depicts the formation of lipid coated particles of the present invention and patterning on glass slides. Tissue Factor (TF); L-α-phosphatidylcholine (PC) and L-α-phosphatidylserine (PS); DHPE (Texas red 1,2-dihexadecanoyl-sn-glycero-3-phosphoethanolamine); 3-[(2-Aminoethyl-amino)propyl]trimethoxysilane (APTMS); Polydimethylsiloxane (PDMS).

In a further aspect, the lipid coated particles are immobilized and patterned to the substrate surface. The patterning may be achieved by a subtractive technique such as microblotting or a lift-off process such as microstenciling. In regards to microblotting, a blotting device may be loaded onto a mechanical press and lowered onto the substrate surface comprising a plurality of the lipid coated particles until the blotting device is in full contact with the substrate surface comprising the immobilized lipid coated particles. Once the blotting device is removed, defined sections and/or areas (i.e. the resulting pattern) of the immobilized lipid coated particles remain on the substrate surface (see FIG. 4). The defined sections and/or areas may be of any geometric shape including but not limited to circular shape, square shape, oval shape, rectangular shape or unshaped and combinations thereof. A circular shape may be referred to as a "spot". Each defined section and/or area is comprised of a plurality of the lipid coated particles. In each defined section and/or area, there is at least more than one lipid coated particle. Preferably, there are hundreds to thousands of lipid coated particles present in each defined section and/or area. The number of individual lipid coated particles within each defined section and/or area can vary and can be in a range from 1 to about 1,000,000 individual lipid coated particles. It is possible for the defined section and/or area to be comprised of a single lipid coated particle. As used herein a plurality of lipid coated particles refers to at least more than one lipid coated particle. The diameter of each defined section and/or area can vary as determined by the patterning method. One or more defined sections and/or areas may result depending on the patterning method. At least one defined section and/or area comprising a plurality of the lipid coated particles results depending on the pattern. The number of defined sections and/or areas found on the substrate surface can vary as determined by the patterning method, the composition of the lipid bilayer and the measurement being taken. The number of defined sections and/or areas can be from about 1 to 1000 defined sections and/or areas. The spacing between two or more defined sections and/or areas of the plurality of the lipid coated particles on the substrate surface may vary depending on the pattern. As an example, the space between two of the defined sections and/or areas may be about 1 μm apart to about 1 mm apart. Each lipid coated particle within the defined section and/or area is smaller than the diameter of the microfluidic channel itself.

The width of the substrate surface comprising the immobilized lipid coated particles may vary depending upon the size of the microfluidic channel. In some embodiments the width may be about 10 micrometers (μm), about 20 μm, about 30 μm, about 40 μm, about 50 μm, about 100 μm, about 150 μm, about 200 μm, about 250 μm, about 300 μm, about 350 μm, about 400 μm, about 450 μm, about 500 μm, about 600 µm, about 700 µm, about 800 µm, about 900 µm or about 1000 µm. The actual width of the substrate surface can have a greater or lesser size without departing from the scope of the present invention.

After the plurality of the lipid coated particles are immobilized and patterned, the particles are integrated into at least one microfluidic channel by aligning either manually, such as by using alignment marks made on the substrate surface, or having posts on the substrate that align with holes that can be found on the microfluidic device or by other methods known to those of skill in the art. Once aligned, the substrate and the device are bonded. Such bonding method includes but is not limited to vacuum assisted bonding.

In a further embodiment, the microfluidic device has the capability of hydrodynamic focusing. Additional buffer, such as HEPES buffered saline (HBS) may be infused through additional side channels of the device to provide focusing of the sample, such as a sample of a blood product, which is perfused through a middle channel. As the buffer solution is perfused in from the side it forces the sample to flow in the middle part of the channel. This design prevents edge effects, most notably, the accumulation of the deposition in the corners of the channel of the sample and/or sample product (see FIG. 5B).

Once the device is produced, in accordance with at least some embodiments of the present invention, the microfluidic device may be hygienically sealed in a sterile environment (e.g. hermetic plastic package) such that the microfluidic device can be distributed as a clot testing kit to medical personnel and other interested parties. In addition, the substrate surface comprising the lipid coated particles can be kept in an aqueous environment. Accordingly, prior to hermetically sealing the microfluidic device in a sterile environment, an aqueous solution may be injected into the hermetic packaging prior to the final sealing. Alternatively, the substrate surface may be kept in a dry environment.

Another embodiment of the invention is a microfluidic channel through which a blood product is capable of flowing. The channel may comprise at least one substrate provided as part of at least a portion of one surface of the channel. The substrate surface comprises a plurality of the lipid coated particles of the invention. These particles comprise at least one functional molecule that is embedded in the lipid coating the particle. The functional molecule is as defined herein. As used herein the term blood product refers to whole blood, plasma, platelet rich plasma (defined as having no red or white blood cells, while containing plasma and platelets), and platelet poor plasma (defined as having no platelets). The blood product of the present invention may be from an individual, such as whole blood or plasma taken from an individual or the blood product may be synthetically produced by methods known in the art.

In accordance with at least some embodiments of the present invention, once the microfluidic device has been prepared, one or more blood component samples can be passed or perfused through the microfluidic channels of the device under flow conditions to evaluate the blood product for coagulation products associated with at least one of the functional molecules of the coated lipid particles. As noted previously, the functional molecules may be one or more transmembrane proteins including but not limited to tissue factor, thromobomodulin, endothelial cell protein C receptor, glycoprotein IIb/IIIa, glycoprotein VI, glycoprotein Ib/IX/V, P-selectin, glycoprotein IV, CD9, platelet endothelial cell adhesion molecule (PECAM-1), Ras-related protein 1b (rap1b), c-type lectin-like receptor 2 (CLEC-2), intracellular adhesion molecule 1 (ICAM-1), intracellular adhesion molecule 2 (ICAM-2) and combinations thereof. In a preferred embodiment, the functional molecule initiates coagulation, such a tissue factor. In another embodiment, the functional molecule inhibits coagulation, such as thrombomodulin.

The flow conditions and rate can be defined by the user of the device. Preferably, the flow conditions simulate hemodynamic conditions of an individual for which the blood product is obtained from. The flow conditions may include a wall shear rate of in the range of about 50 $sec^{-1}$ to about 2600 $sec^{-1}$, which corresponds to the normal range shear rates in the human vasculature. The flow conditions may also include wall shear rates in a range from zero up to about 500,000 $sec^{-1}$ for testing conditions in which the pathological flow conditions exist. Pathological flow conditions may occur if the flow has been retarded, as in the case of individuals diagnosed deep vein thrombosis, or if blood is forced to pass through a partially occluded or stenosed vessel, as in the case of individuals diagnosed with atherosclerosis.

As the one or more blood component samples are perfused through the microfluidic channel and over the substrate surface comprising a plurality of the lipid coated particles comprising one or more functional molecules of the present invention, and the sample is perfused at a user defined flow rate, coagulation products can be detected as one or more coagulation products associates with the coated lipid particles comprising the functional molecule. Coagulation products include but are not limited to thrombin, fibrin, thrombin-antithrombin complex, fibrinopeptide A, fibrinopeptide B, D-dimer, prothrombin fragment 1+2, activated factor X, activated factor V, activated factor VIIIa, activated factor IXa, activated factor XIa, activated factor XIIa, activated protein C, activated protein S, and mixtures thereof. The coagulation products may be detected and/or measured by various methods including but not limited to brightfield microscopy, darkfield microscopy, fluorescence microscopy, multi-photon excitation, second harmonic generation, third harmonic generation, atomic force microscopy, scanning electron microscopy, and absorbance. For example, thrombin and/or fibrin amounts can be detected and/or measured by using a fluorescent substrate such as boc-VPR-AMC for thrombin and for fibrin by adding exogenous fibrinogen with a fluorescent label. Thrombin generation could also be indirectly detected and/or measured by measuring collecting the effluent at the outlet of the device and measuring the concentration of thrombin-antithrombin complex (TAT) or the release of fibrinopeptides (peptides that are released off of fibrinogen following cleavage by thrombin). Fibrin could also be detected and/or measured using a fibrin specific antibody or by other microscopy techniques such as differential contrast, phase contrast and Hoffman modulation. Any of the other transmembrane protein could be detected and/or measured in similar ways to those described above. An individual's result may be compared to results that have been obtained under identical conditions using plasma pooled from normal donors (i.e. normal pooled plasma (NPP) which is plasma that has been pooled from a number of normal donors (donors without known blood coagulation conditions)). The NPP can be plasma standards that are available commercially. Additionally, an individual's results can be compared to results that have been obtain under identical conditions using factor deficient plasmas such as factor II (prothrombin), factor VIII, factor IX, factor and factor XI deficient plasmas.

Another embodiment of the present invention relates to a method for determining an individual's coagulation potential, comprising perfusing an individual's blood product (such as plasma) over the substrate surface comprising the coated lipid particles of the present invention and one or more functional molecules, wherein one or more coagulation products associate with the lipid particles; and detecting one or more coagulation products associated with the lipid particles. In one aspect, the lipid particles comprise functional molecules. The functional molecules can initiate coagulation or can inhibit coagulation. In a preferred aspect, the functional molecules are tissue factor and thrombomodulin. The flow rate of the blood product can be a rate which mimics hemodynamic conditions of the individual. The normal range of shear rates in the human vasculature is about 50 to 2600 $sec^{-1}$.

Another embodiment of the invention relates to a method for determining an individual's response to an agent comprising perfusing the individual's blood product (such as plasma) over the substrate surface comprising the coated lipid particles of the present invention and one or more functional molecules wherein one or more coagulation products associate with the lipid particles; and detecting one or more coagulation products associated with the lipid particles. In one aspect, the agent is an anticoagulant agent or coagulating agent.

In still another embodiment, the invention relates to a method to diagnose and/or monitor an individual for bleeding comprising perfusing the individual's blood product (such as plasma), over the substrate surface comprising the coated lipid particles of the present invention and one or more functional molecules wherein one or more coagulation products associate with the lipid particles; and detecting one or more coagulation products associated with the lipid particles.

In yet another embodiment, the invention relates to a method to determine the dose of one or more anticoagulation agents or coagulation agents to be administered to an individual comprising perfusing the individual's blood product (such as plasma), over the substrate surface comprising the coated lipid particles of the present invention and one or more functional molecules, wherein one or more coagulation products associate with the lipid particles; and detecting one or more coagulation products associated with the lipid particles.

Yet another embodiment relates to a method to screen for anticoagulation agents or coagulation agents comprising perfusing the individual's blood product (such as plasma), over the substrate surface comprising the coated lipid particles of the present invention and one or more functional molecules, wherein one or more coagulation products associate with the lipid particles; and detecting one or more coagulation products associated with the lipid particles.

Still another embodiment relates to a method to screen for coagulation agents comprising perfusing the individual's blood product (such as plasma), over the substrate surface comprising the coated lipid particles of the present invention and one or more functional molecules, wherein one or more coagulation products associate with the lipid particles; and detecting one or more coagulation products associated with the lipid particles.

The individual in the invention can include any mammal, including human and non-human mammals.

The following experimental results are provided for purposes of illustration and are not intended to limit the scope of the invention.

EXAMPLES

Example 1

This example demonstrates the fabrication of lipid coated particles of the present invention to detect fibrin formation.

In order to initiate fibrin formation in the plasma-based model for coagulation using the microfluidic device of the present invention, silica microbeads are used to simulate the catalytic activity of platelets. Once the silica beads are made hydrophilic, their surfaces are coated with lipid bilayers, which contain varied concentrations of functional molecules such as tissue factor (TF) and thrombomodulin (TM) that initiate and inhibit coagulation. The composition of the lipid bilayer can be manipulated to mimic the surface of various cell types. This is accomplished by mixing different ratios of phospholipids such as phosphatidylserine (PS), phosphatidylcholine (PS), and phosphatidylethanolamine (PE). A description of the fabrication of silica beads and coating them with phospholipids is found below:

1. Weigh or measure out 2.1 mL of deionized water, 15.4 mL of anhydrous ethanol, and 6.5 mL of ammonium hydroxide in a plastic container.
2. Stir for 10 minutes with a magnetic stirrer, and then add 1.5 mL tetraethyl orthosilicate (TEOS) dropwise.
3. Stir the solution for 2 hours at the room temperature.
4. After 2 hours, centrifuge the precipitated silica beads, and wash in ethanol 4 times.
5. Resuspend the bead solution of 400 mg in 1 ml of deionized water.
6. Dilute the silica particles to a concentration of 5 mg/ml in DI water
7. Add hydrogen peroxide and HCl solution to the mixture to final concentrations of 4% vol and 0.4 M, respectively.
8. Stir the solution at 85° C. for 10 minutes, then cool the mixture to room temperature.
9. Wash the solution of beads by centrifuging the beads at 2000 RPM for 5 minutes and re-suspending in buffered saline to wash the beads. Repeat 5 times
10. Pipette 200-500 uL of the silica bead in a microcentrifuge tube and centrifuge the silica beads at 2000 RPM for 3 minutes.
11. Pipette out the supernatant buffer without drying out the silica beads and add 100 uL of liposome. Vortex the mixture until the silica beads are re-suspended in the lipid solution
12. Incubate the lipid-bead mixture for 24 hours at 4° C. to allow the lipid bilayers to rupture on the silica bead surfaces
13. Centrifuge the silica beads at 2000 RPM for 5 minutes, then pipette off the supernatant solution. Do not dry out the beads.
14. Rinse the beads thoroughly with a 1× HBS buffer
15. Re-suspend the lipid coated silica beads to concentration of 1 mg/mL and store at 4° C. until ready to use.

Example 2

This example demonstrates an example of the patterning of lipid coated particles of the present invention.

Once the lipid coated particles are made as described in Example 1, they need to be immobilized and patterned onto a substrate. The immobilization of the particles can rely on methods such as covalent bonds (e.g. streptavidin-biotin), electrostatic interactions, or hydrogen bonding. The patterning may be achieved either by a subtractive technique such as microblotting or a lift-off process such as a microstencil. A microblotting technique is described below:
1. Obtain a 100 µg/mL solution of silica beads functionalized with lipid bilayer as explained in Example 1.
2. Incubate a 100 µg/mL solution of the lipid coated particles in HBS buffer onto and APTES functionalized glass slide for 1 hour at room temperature. Wash substrates three times in HBS buffer to remove unbound beads.
3. Place glass slide into a 6-inch petri dish with 100 mL of deionized 18 MΩ water.
4. Load blotting devices onto a customized mechanical press and lower onto the slide until the device is in full contact with the slide. The device is contacted on the slide for 3 minutes.
5. Thoroughly rinse the patterned slide in PBS or HBS for 5 min. Store the patterned slide in buffer until use in the flow assay.

Example 3

This example demonstrates an example of the integration of the lipid coated particles into microfluidic channels of the present invention.

After immobilizing and/or patterning the lipid coated particles, the microfluidic device of the present invention is aligned and bonded to the substrate. Because the lipid bilayers on the lipid coated particles should remain hydrated, this step should be done while the substrate is immersed or covered in buffer solution. The device may be aligned either manually or using alignment marks on the substrate. Once in contact, the device may be bonded to the substrate by vacuum assisted bonding.

Example 4

The example demonstrates how to measure coagulation under flow conditions.

The procedure for the assay itself using the microfluidic device of the present invention comprises perfusing plasma through the microfluidic channels and over the plurality of the lipid coated particles at a user defined flow rate. Coagulation can be monitored by a variety of optical methods: (1) fibrin generation by brightfield microscopy (phase contrast, Hoffman modulation contrast, differential interference contrast), (2) fibrin generation by fluorescence microscopy (epifluorescence or confocal), which requires that either some fibrinogen is labeled with a fluorophore or the inclusion of a fibrinogen or fibrin fluorescence labeled antibody into the plasma, (3) fibrin generation by nonlinear optical methods (two photon excitation, second harmonic generation, third harmonic generation), (4) thrombin generation by monitoring the fluorescence or absorbance of a thrombin substrate (e.g. boc-VPR-AMC), (5) thrombin generation by measuring thrombin-antithrombin (TAT) complex, (6) fibrin deposition by measurement of the D-dimer following digestion by plasmin, (7) fibrin generation by measurement of fibrinopeptides A and B.

Example 5

This example demonstrates the use of the microfluidic device of the present invention to measure transient fibrin deposition and thrombin generation. The Inventors demonstrate that for a given Tissue Factor (TF) concentration, flow profoundly influenced fibrin deposition, fiber diameter, fiber orientation and local thrombin concentration. The microfluidic device can also be used to investigate the effects of different factor deficiencies on the dynamics of fibrin production and thrombin generation.

These findings suggest that for significant fibrin formation to occur, coagulation reactants and products must be protected from transport away from a clot either by a reduction in shear rate (i.e. occlusion or within secondary flows downstream of stenosis) or within the interstitial spaces of a platelet aggregate.

Figure 5:
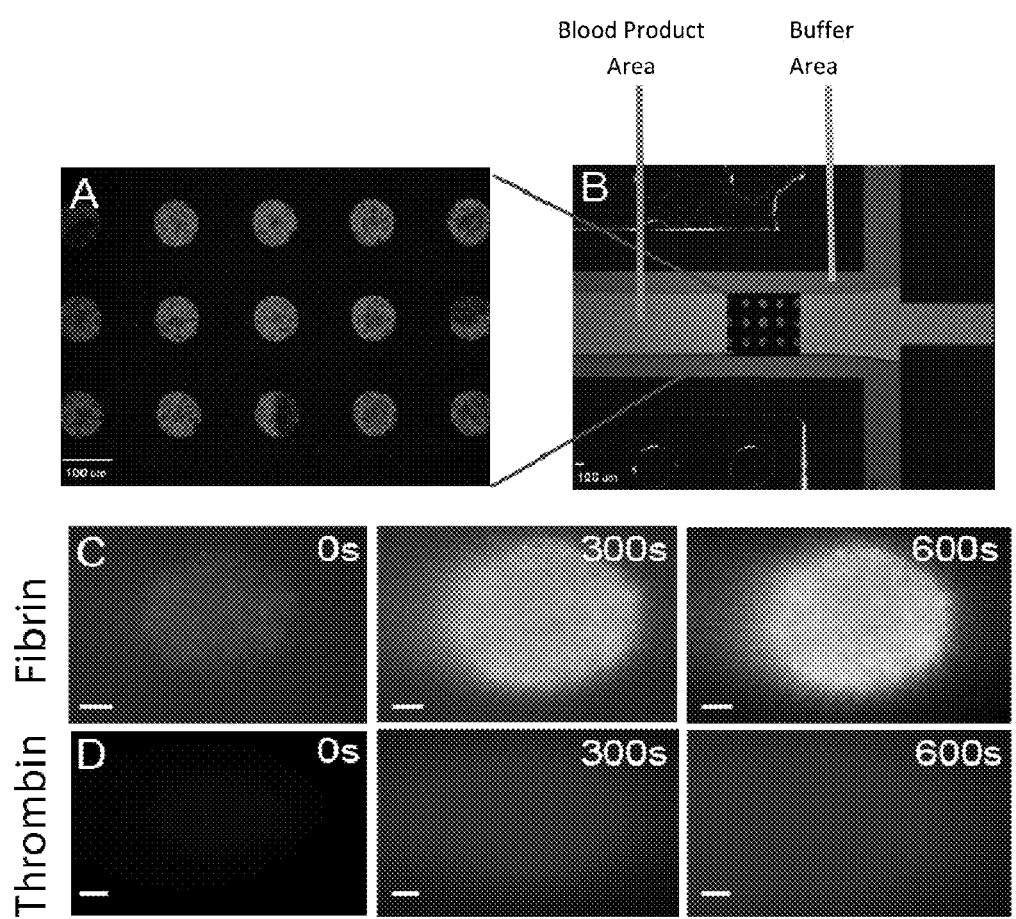
FIG. 5A depicts 100 µM patterned Tissue Factor lipid coated particles. A plurality of lipid coated particles is found within each spot.
FIG. 5B depicts a microfluidic device with hydrodynamic focusing which is used to force Alexa 488-labelled plasma (lightest shaded region indicated as the "Blood Product Area") to flow in the center over the patterned lipid coated particles in the spots, while bounded on the side by Texas red labeled buffer (mid-shaded regions adjacent to the lightest shaded regions indicated as the "Buffer Area").
FIG. 5C depicts fibrin that is formed over the lipid coated particle spots of FIG. 5B over a 10 minute perfusion of plasma. 0 s represents start of perfusion, 300 s represents 300 seconds after the start of perfusion and 600 s represents 600 seconds (or 10 minutes) after the start of perfusion.
FIG. 5D depicts thrombin generation over the lipid coated particle spots of FIG. 5B as measured by a blue signal that is emitted when the thrombin substrate boc-VPR-AMC is cleaved over a 10 minute perfusion of plasma. 0 s represents start of perfusion, 300 s represents 300 seconds after the start of perfusion and 600 s represents 600 seconds (or 10 minutes) after the start of perfusion.
Figure 6A:
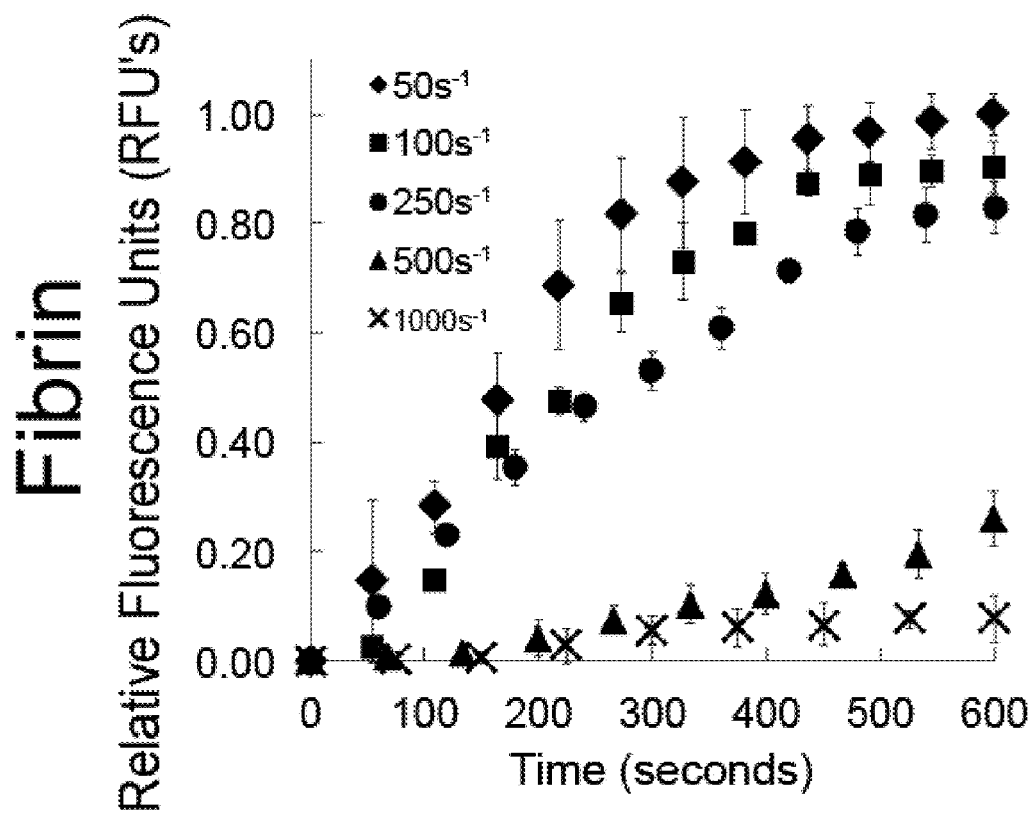
FIG. 6A depicts fibrin generation after normal pooled plasma (NPP) was perfused over TF lipid coated particles using the microfluidic device of the present invention, wherein the TF concentration was 50 molecules/µm$^2$ at wall shear rates of 50, 100, 250, 500 and 1000 s$^{-1}$. Relative Fluorescence Units (RFUs) were determined in real-time using three metrics to quantify the dynamics of fibrin generation (i) the lag time to fibrin fiber generation, (ii) the maximum fibrin density, and (iii) the rate of fibrin generation.
Figure 6B:
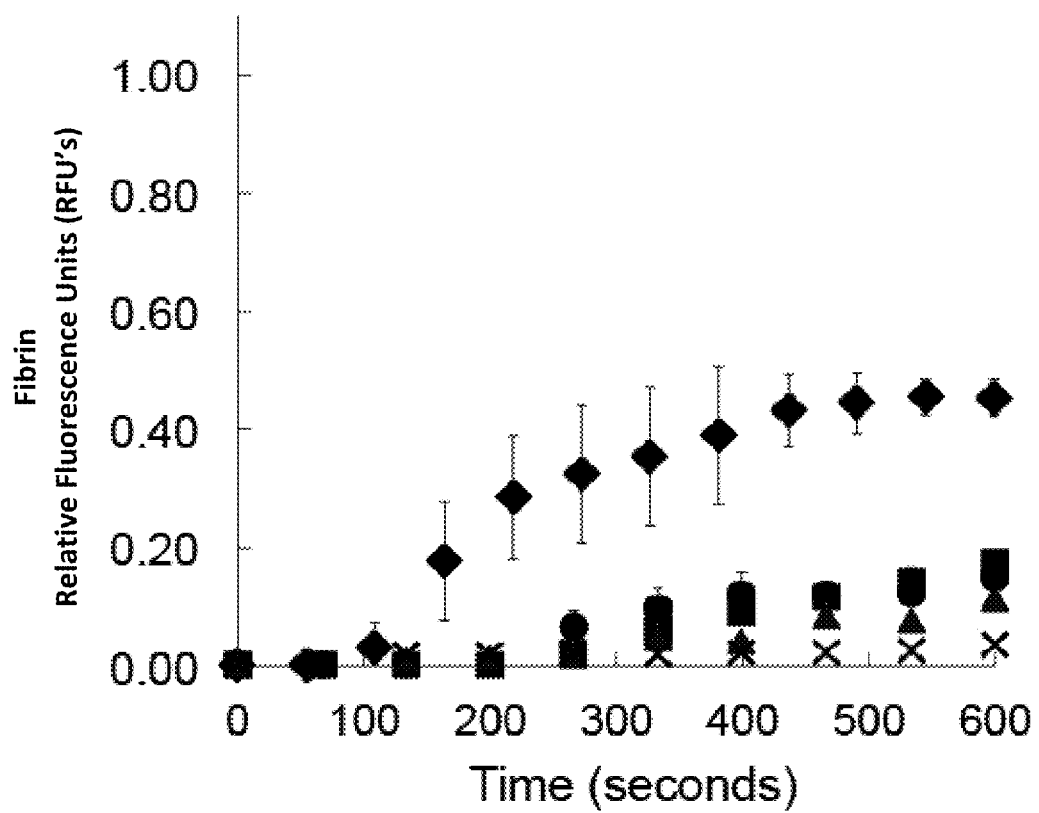
FIG. 6B depicts fibrin generation after normal pooled plasma (NPP) was perfused over TF lipid coated particles using the microfluidic device of the present invention, wherein the TF concentration was 5 molecules/µm$^2$ at wall shear rates of 50, 100, 250, 500 and 1000 s$^{-1}$. Relative Fluorescence Units (RFUs) were determined in real-time using three metrics to quantify the dynamics of fibrin generation (i) the lag time to fibrin fiber generation, (ii) the maximum fibrin density, and (iii) the rate of fibrin generation.
Figure 6C:
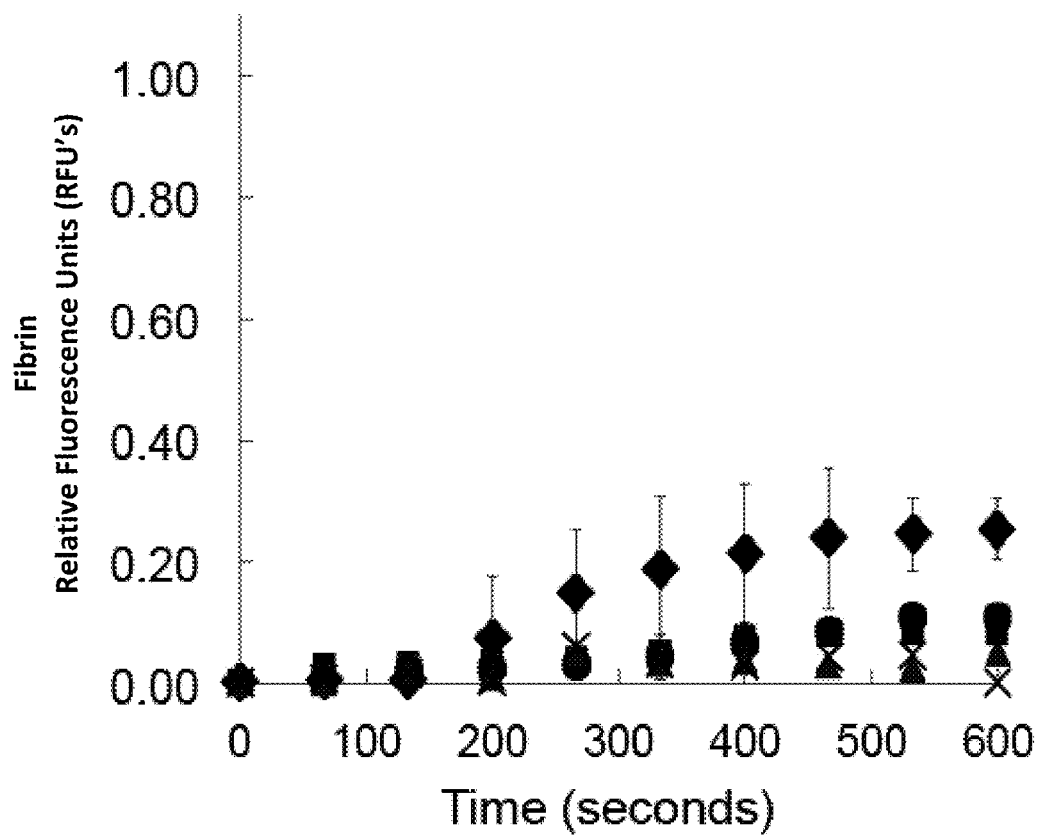
FIG. 6C depicts fibrin generation after normal pooled plasma (NPP) was perfused over TF lipid coated particles using the microfluidic device of the present invention, wherein the TF concentration was 0.5 molecules/µm$^2$ at wall shear rates of 50, 100, 250, 500 and 1000 s$^{-1}$. Relative Fluorescence Units (RFUs) were determined in real-time using three metrics to quantify the dynamics of fibrin generation (i) the lag time to fibrin fiber generation, (ii) the maximum fibrin density, and (iii) the rate of fibrin generation.
Figure 6D:
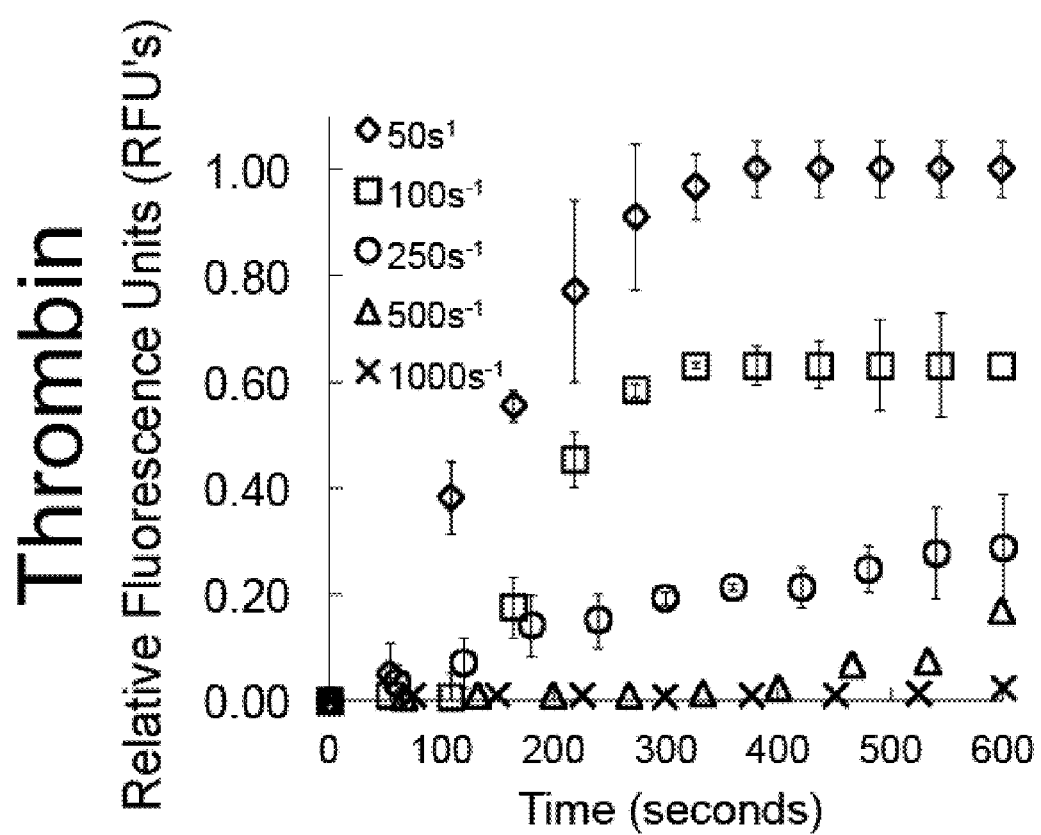
FIG. 6D depicts thrombin generation after normal pooled plasma (NPP) was perfused over TF lipid coated particles using the microfluidic device of the present invention, wherein the TF concentration was 50 molecules/µm$^2$ at wall shear rates of 50, 100, 250, 500 and 1000 s$^{-1}$. Relative Fluorescence Units (RFUs) were determined in real-time using three metrics to quantify the dynamics of thrombin generation (i) the lag time to thrombin generation, (ii) the maximum thrombin fluorescence, and (iii) the rate of thrombin generation.
Figure 6E:
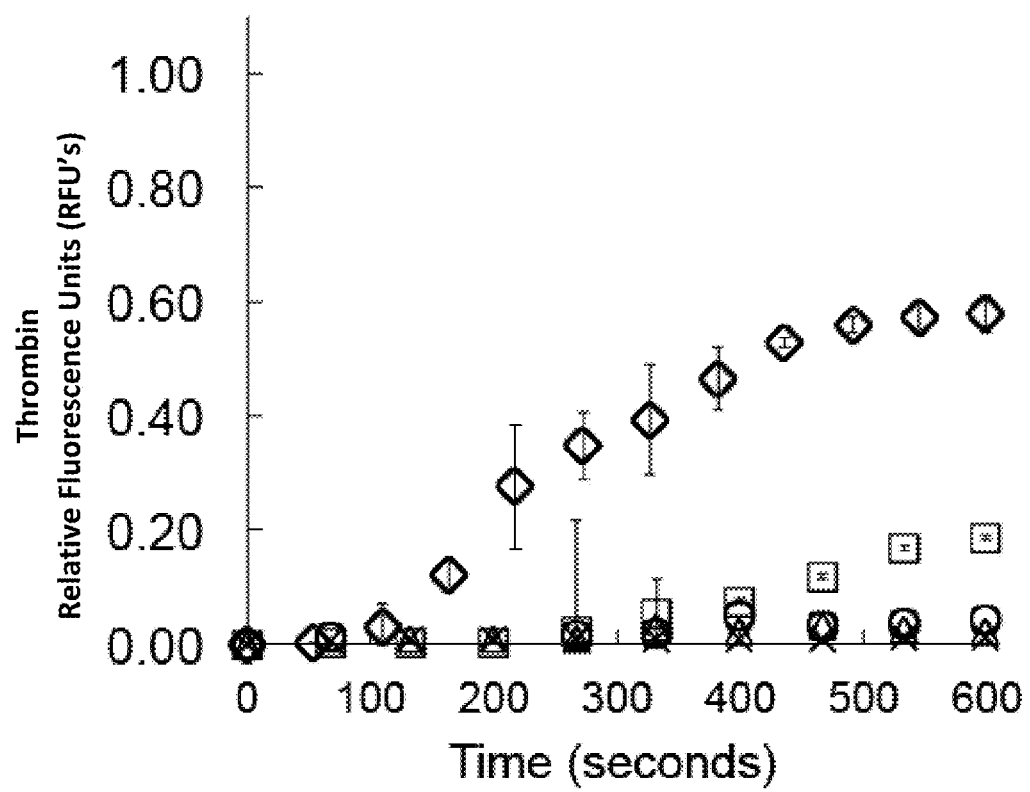
FIG. 6E depicts thrombin generation after normal pooled plasma (NPP) was perfused over TF lipid coated particles using the microfluidic device of the present invention, wherein the TF concentration was 5 molecules/µm$^2$ at wall shear rates of 50, 100, 250, 500 and 1000 s$^{-1}$. Relative Fluorescence Units (RFUs) were determined in real-time using three metrics to quantify the dynamics of thrombin generation (i) the lag time to thrombin generation, (ii) the maximum thrombin fluorescence, and (iii) the rate of thrombin generation.
Figure 6F:
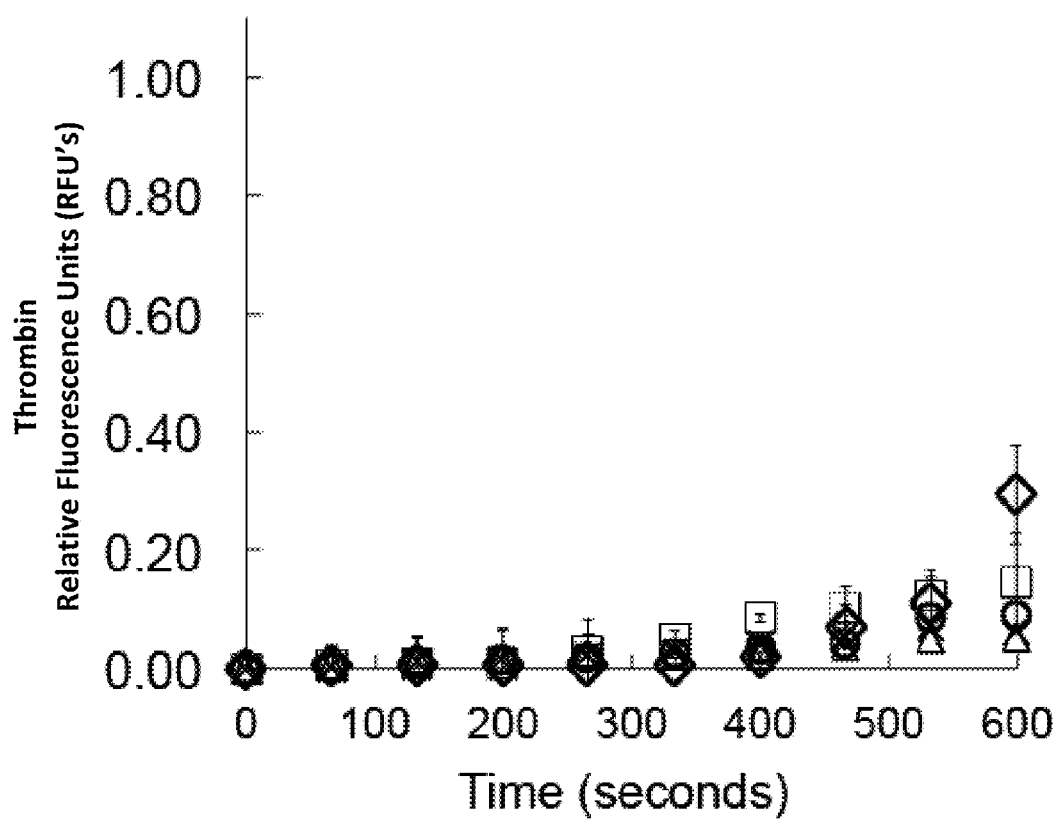
FIG. 6F depicts thrombin generation after normal pooled plasma (NPP) was perfused over TF lipid coated particles using the microfluidic device of the present invention, wherein the TF concentration was 0.5 molecules/$\mu m^2$ at wall shear rates of 50, 100, 250, 500 and 1000 $s^{-1}$. Relative Fluorescence Units (RFUs) were determined in real-time using three metrics to quantify the dynamics of thrombin generation (i) the lag time to thrombin generation, (ii) the maximum thrombin fluorescence, and (iii) the rate of thrombin generation.

Preparation of TF Lipid Coated Particles and Assay Conditions Using the Microfluidic Device TF bearing lipid coated particles were synthesized by coating 1 µm silica beads with 0.5, 5, or 50 molecules TF/µm$^2$ in a lipid bilayer (PS:PC 30:70). The lipid coated particles were patterned as 100 µm spots on a glass substrate using a microblotting technique. (FIG. 5A). Normal pooled plasma (NPP), factor deficient plasmas FII, FVIII, FX and FXI were perfused over the TF spots at wall shear rates of 50, 100, 250, 500 and 1000 sec$^{-1}$ for 10 min. (FIG. 5B). Fibrin formation and thrombin generation were measured in real-time by epifluorescence using labeled fibrinogen and the thrombin substrate boc-VPR-AMC, respectively. (FIGS. 5C-5D). Following the assay, fibrin gels were either (i) fixed and further imaged by confocal or scanning electron microscopy or (ii) digested by plasmin to measure the rate of lysis and to quantify the amount of fibrin deposited using a D-dimer ELISA.

Shear Rate Dependent Fibrin Deposition and Thrombin Generation

NPP was perfused over surface TF concentration of 0.5, 5 and 50 molecules/µm$^2$ at wall shear rates of 50, 100, 250, 500 and 1000 sec$^{-1}$. For each experiment, fibrin deposition and thrombin generation were monitored in real-time. Fibrin deposition and thrombin generation decreased with increasing wall shear rate and decreasing TF concentration. (FIGS. 6A-6F). Three metrics were used to quantify the dynamics of fibrin formation and thrombin generation; (i) the lag time to fibrin fiber and thrombin generation, (ii) the maximum fibrin density and thrombin fluorescence, and (iii) the rate of fibrin and thrombin generation.

At a given TF concentration either of 50, 5 and 0.5 molecules/µm$^2$ there was a decrease in the lag time and fibrin generation rate with increasing wall shear rate. As a result of the decrease in the rate of fibrin production, the maximum fibrin deposited also decreased with an increase in shear rate. The thrombin generation followed the same trend as the fibrin deposition.

At the highest shear rates and lowest tissue factor concentration, no fibrin fibers were observed in the time period of the experiments therefore there was a subthreshold amount thrombin produced to induce fibrin formation.

The cumulative fibrin deposited on all spots over the 10 minute flow assay was measured by D-dimer concentration following plasmin digestion. The threshold nature of fibrin formation is evident at all three TF concentrations. For 5 and 50 molecules/µm$^2$, fibrin formation was supported at wall shear rates less than or equal to 250 s$^{-1}$. For 0.5 molecules/µm$^2$, fibrin formation was supported at wall shear rates of less than or equal to 100 s$^{-1}$.

Figure 7:
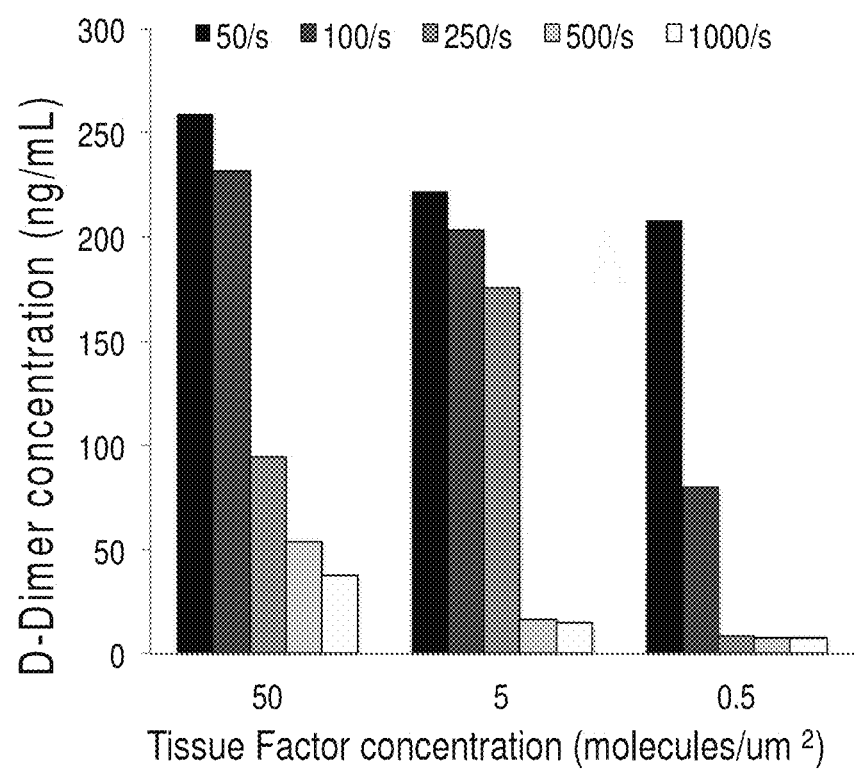
FIG. 7 shows the results of a D-dimer analysis of the cumulative fibrin deposited (generated) as described in FIG. 6A-6C on all the spots comprising a plurality of the TF lipid coated particles as measured by D-dimer concentration following plasmin digestion. The wall shear rates are provided at the top of the graph.

After plasma perfusion, the fibrin fibers produced on the TF spots were digested with plasmin over time and monitored by the decrease in fluorescence intensity over time. The analysis of the rate of digestion shows that the fibers produced at the lowest shear rate digested the fastest (46.1 RFU/s) (i.e. relative fluorescence units/second), while the fibers produced at the highest shear rate digested the slowest (17.3 RFU/s). Overall, the D-dimer analysis shows a decrease in the quantity of D-dimer fragments as shear rate is increased and tissue factor concentration is decreased (FIG. 7). The D-Dimer results also confirm that at the lowest TF concentration and the highest shear rates there was little or no fibrin observed to be produced because the signals were the same as that of the ELISA background.

Cross-Talk Between Spots

In each assay there were 142 35 11 fibrin(ogen) lipid coated particle spots with a spot-to-spot distance of 200 µm. There was an increase in accumulation of fibrin from upstream to downstream spots at shear rates of 50 s$^{-1}$ and 100 s$^{-}$. There were also vertical spot to spot interactions at all shear rates where fibrin was produced, depending on the distance from the leading spot upstream. Fibrin monomers were being transported downstream with flow. This trend was evident at all shear rates where fibrin was produced.

Shear Rate Effects on Fibrin Morphology

Figure 8A:
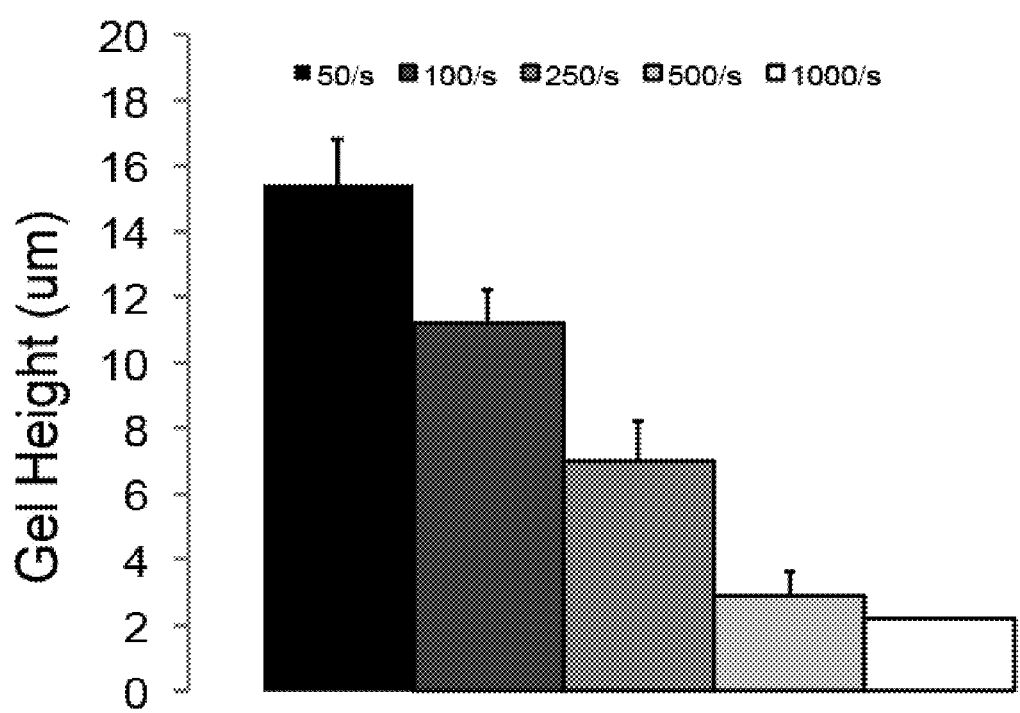
FIG. 8A shows the fiber height of the fibrin fibers that accumulated on the individual spots from the assay described in FIGS. 6A-6C wherein the fiber height is provided for each of the wall shear rates of 50, 100, 250, 500 or 1000 $s^{-1}$ to show the shear rate effects with distribution of the fibrin fibers.
Figure 8B:
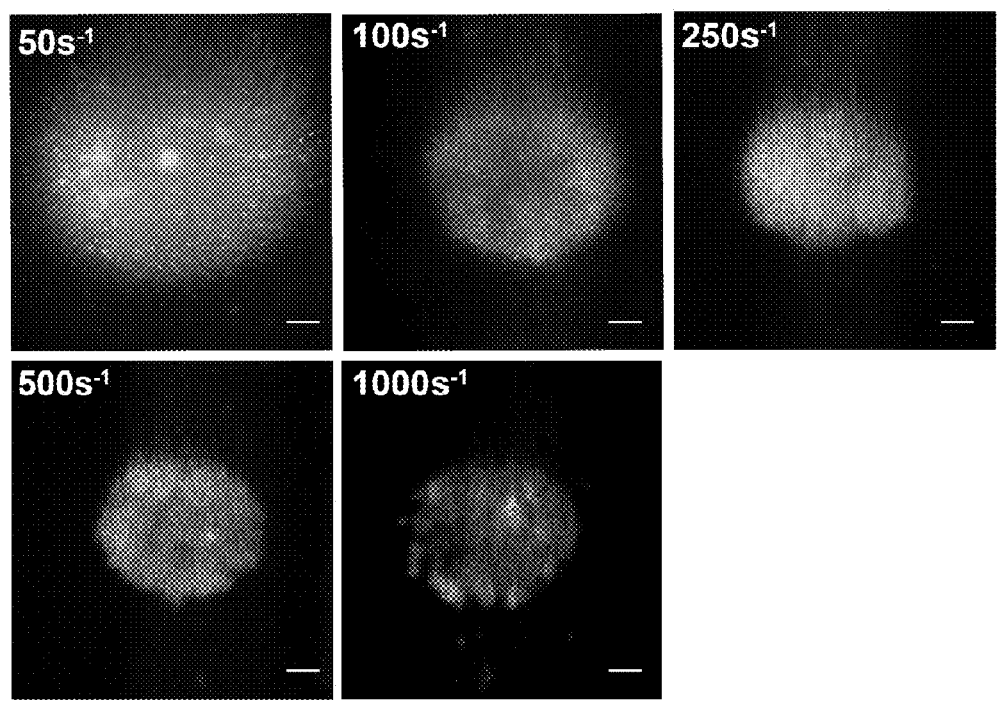
FIG. 8B shows final fluorescence images showing a decrease in fibrin fiber density and intensity with an increase in shear rate (scale bars=20 um) from the assay described in FIGS. 6A-6C.
Figure 8C:
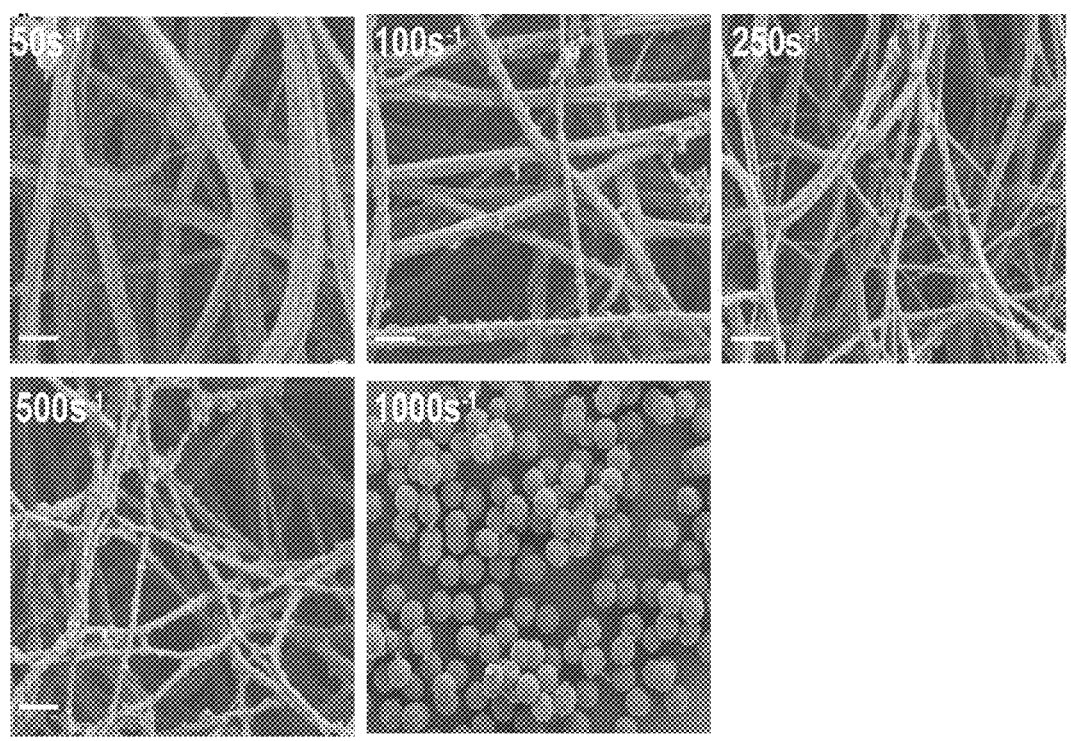
FIG. 8C shows scanning electron micrographs of fibrin diameter decreasing with an increase in shear rate from the assay described in FIGS. 6A-6C.

The final gel-height of the fibers accumulated on the individual spots also showed the same trend as the fibrin deposition (FIG. 8A). The lowest shear rate had a height of 15.3 µm, while the highest shear rate had a height of 2.1 µm. Fibrin fibers align in the direction of flow in a shear rate dependent manner (FIG. 8B). At 50 s$^{-1}$ and 100 s$^{-1}$, the fibers were isotropically oriented in a starburst pattern. With increasing wall shear rates of 250 s$^{-1}$ to 1000 s$^{-1}$, the fibers become more orientated with flow. Fibrin fiber diameter also decreases with increasing wall shear rate (FIG. 8C). The lowest shear rate had the largest diameters, with individual fibers appearing to be composed of smaller fibers joint together to form bigger ones. At the highest shear rate, the spots were scanned and no discernable fibers could be found under the scanning conditions used.

The Effect of FVIII, FIX, and FXI Deficiencies on Fibrin Deposition

Figure 9:
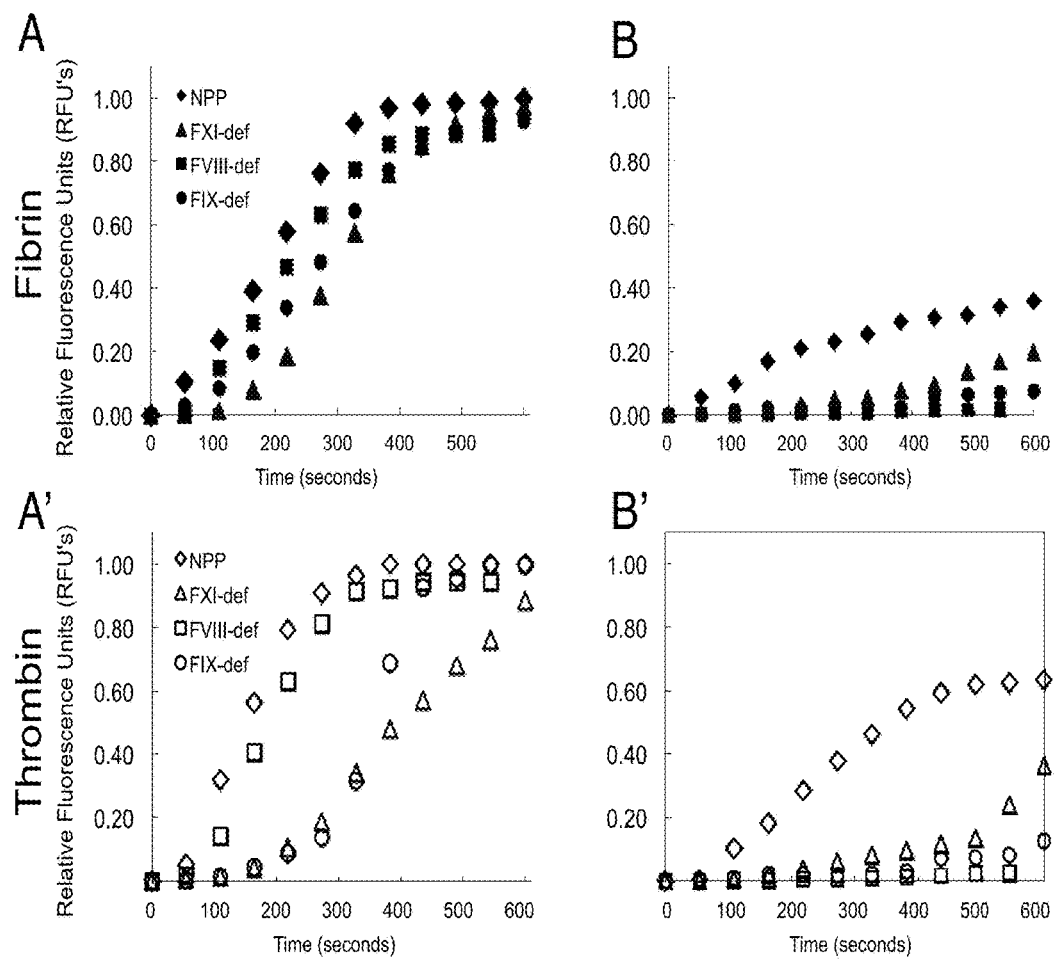
FIG. 9A shows fibrin generation for factor deficient plasma at 50 $s^{-1}$ and TF concentration of 50 molecules/$\mu m^2$ using the assay described in FIGS. 6A-6C. Normal pooled plasma (NPP); plasma deficient with factor XI (FXI-def); plasma deficient with factor VIII (FVIII-def); and plasma deficient with factor IX (FIX-def).
FIG. 9B shows fibrin generation for factor deficient plasma at 5 $s^{-1}$ and TF concentration of 5 molecules/$\mu m^2$ using the assay described in FIGS. 6A-6C. Normal pooled plasma (NPP); plasma deficient with factor XI (FXI-def); plasma deficient with factor VIII (FVIII-def); and plasma deficient with factor IX (FIX-def).

NPP and FII, FVIII, FIX, FX and FXI deficient plasma were perfused in the microfluidic device at the conditions of low shear rates and high TF concentrations. As controls, FII and FX deficient plasmas showed no visible fibrin production at 50 s$^{-1}$ or at any other shear rates tested. At 50 molecules/µm$^2$, there was a slightly prolonged lag time for FVIII, FIX and FXI deficient plasma compared to NPP, however the final fibrin deposition was similar (FIG. 9A). The difference between NPP and these deficient plasmas at high TF concentrations was more evident in the thrombin generation data (FIG. 9A'). FVIII deficient plasma was indistinguishable from NPP. FIX deficient plasma had a reduced rate of thrombin generation. FXI deficient plasma had a prolonged lag time compared to NPP. At low TF concentration (5 molecules/µm$^2$), there was reduced fibrin deposition and thrombin generation for FVIII, FIX, and FXI deficient plasmas compared to NPP. There was almost a complete absence of fibrin for FVIII and FIX deficient plasma, while the fibrin deposition for the FXI deficient plasmas was significantly reduced. The trends for thrombin generation were similar to fibrin deposition at low TF (FIGS. 9B and 9B').

Materials and Methods and Data Analysis for Example 5

Materials: L-α-phosphatidylcholine (PC) and L-α-phosphatidylserine (PS) were purchased from Avanti Polar Lipids (Alabaster, Ala., USA). Texas red 1,2-dihexadecanoyl-sn-glycero-3-phosphoethanolamine (DHPE) was purchased from Invitrogen (Carlsbad, Calif., USA). Bio-Beads SM-2 were purchased from BioRad Laboratories (Hercules, Calif., USA). Sodium deoxycholate was purchased from CalBiochem (Gibbstown, N.J., USA). Boc-Val-Pro-Arg-MCA [t-Butyloxyl-carbonyl-L-Valyl-L-Prolyl-L-Arginine-4-Methyl-Coumaryl-7-Amide], was purchased from Peptide Institute Inc, Osaka, Japan and a 10 mM stock solution was prepared according to manufacturer instruction. Recombinant human tissue factor (TF), IMUBIND tissue factor ELISA and D-Dimer ELISA were from America Diagnostica (Stamford, Conn.), and were used according to the manufacturer's instructions. Plasmin was purchased from Enzyme Research Laboratories (South Bend, Ind.). Normal pooled plasma (NPP) and factor XI, X, IX, VIII, VII and II deficient plasmas were purchased from George King Biomedical (Overland Park, Kans.). Alexa Fluor 488 protein labeling kit (Invitrogen, Carlsbad, Calif., USA) was used to label fibrinogen according to the manufacturers instruction. Polydimethylsiloxane (PDMS) used for microfluidic devices (Dow Corning, Sylgard 184) was purchased from Ellsworth Adhesives (Germantown, Wis.). HEPES buffered saline (HBS, 20 mM HEPES, 150 mM CaCl$_2$, pH 7.4) was made in house. 3-[(2-Aminoethylamino) propyl] trimethoxysilane (APTMS), tetraethyl orthosilicate (TEOS) and all other chemical were purchased from Sigma Aldrich (St. Louis, Mo.).

Preparation of Lapidated Tissue Factor

Recombinant human tissue factor was incorporated into liposomes according to previously developed protocols (Smith and Morrissey, Journal of Thrombosis and Haemostasis, 2:1155-1162). Briefly, PC, PS and DHPE lipids were mixed at a 80:19.5:0.5 molar ratio in chloroform and dried under vacuum for 1 h. The dried film was resuspended in 1 mL of 20 mM sodium deooxycholate in HBS, and allowed to hydrate for 1 h at room temperature. TF was then added to the lipid mixture and incubated for 10 minutes (8700:1 lipid:TF). Detergent was removed from the lipid solution with 50 mg of Biobeads under agitation for 90 min. Next, an additional 350 mg of Biobeads were added to the same solution, and agitated for another 90 minutes. Finally, the beads were allowed to settle and the supernatant TF was collected. The concentration of the lipidated TF was determined by ELISA to be 460 nM.

Preparation of Silica Beads

The Stober process was used to synthesize silica beads used in this study. Tetraethylorthosilicate (TEOS) was added drop wise to a mixture of water, ethanol and ammonium hydroxide, and the solution was stirred for 2 h at room temperature. The resulting solution was centrifuged at 2000 rpm for 5 minutes, washed in ethanol and suspended in HBS buffer. Finally, transmission electron microscopy (TEM) was used to characterize the size distribution of these silica particles as ranging from 800 to 1000 nm.

Preparation of TF Lipid Coated Particles

To promote the formation of lipidated TF on the surface of the 1 µm silica beads, the beads were first made hydrophilic by suspending them at a concentration of 5 mg/ml in 4% peroxide and 0.4 M HCl solution. Then, the suspension was heated to 80-90° C. for 10 min, cooled to 25° C., centrifuged at 2000 rpm for 5 min, washed three times with deionized water and finally re-suspended in HBS buffer. To confirm that the surface chemistry was successful, Fourier transform infrared spectroscopy (FTIR) was used to confirm the presence of deposited surface silanol groups (SiOH groups) on the silica particles. Next, the desired concentration of beads was pipetted from the stirred stock suspension, centrifuged, and the supernatant was replaced by the desired lipidated TF concentration. The suspension was gently vortexed for 30 min. and then allowed to sit undisturbed for 5 min. Finally, the beads were finally centrifuged and washed three times with HBS buffer to remove unbound lipids from the solution.

Microblotting TF Lipid Coated Particles

Clean glass slides were incubated in a 40 wt % APTMS in ethanol solution for 45 minutes. The amine group on the APTMS renders the surface positively charged. The negatively charged TF-coated silica beads were incubated for 4 h on the positively charged glass slides and then rinsed with HBS to remove excess silica beads. Next, a PDMS microblot with 100 µm holes spaced 200 µm center-to-center was used selectively remove beads from the surface. Electrostatic interactions between the beads and the surface provides an adequate attractive force to withstand the shear stresses during the flow assays.

Plasma Flow Assay

A polydimethylsiloxane (PDMS) microfluidic hydrodynamic focusing device (w=1000 µm, g=100 µm) was vacuum-sealed to the glass slide containing the patterned lipid coated particles. Within each channel there was 5×22 array of 100 µm bead spots. HBS was infused through the two side channels to provide the focusing of plasma, which was perfused through the middle channel (Fig. X). The total flow rate (HBS and plasma) through the main channel was set to achieve the desired wall shear rate using the expression: $\gamma = 6 \times Q/H^2 W$ where $\gamma$ is the shear rate, Q is the volumetric flow rate, W is the width and H is the height. As the buffer solution was perfused in from the side (red) it forced the plasma (green) to flow in the middle part of the channel. This design prevents edge effects, notably the preferential accumulation of fibrin deposition in the corners of the channel.

Citrated normal pooled plasma (NPP), FII, FX, FVIII, FIX and FXI deficient plasmas were defrosted at 37° C. immediately before perfusion through the microfluidic flow device. The citrated plasma (400 µL) was re-calcified by adding 20 µL of a solution of $CaCl_2$ (500 mM) and withdrawn with a syringe pump at wall shear rates of 50, 100, 250, 500 and 1000 $s^{-1}$. To monitor fibrin formation, Alexa 488 labeled fibrinogen was added to the plasma at 17.5 µg/mL. Thrombin generation was monitored through the cleavage of a fluorogenic substrate, Boc VPR-AMC.

Data Acquisition and Image Analysis

Fibrin deposition and thrombin generation were measured for 10 minutes, and images were recorded every 50 s by epifluorescence microscopy using a 40× objective. The data was taken starting from the leading spot upstream where the plasma first encountered the lipidated-TF lipid coated particle bead spot pattern. Image J software was used to determine the integrated fluorescence of the fibrin or thrombin generated on single bead spots.

Plasmin Digestion and D-Dimer Level Measurements of Fibrin Deposits

After the plasma perfusion, the heparin wash buffer was used to rinse the channel for 5 min. at the same shear rate as the experiment. Next, a 250 µL plasmin solution (0.48 mg/ml diluted in HBS containing 1 mM Tris/HCl, pH 7.4) was perfused through the microfluidic channel at a flow rate of 5 µL/min for 10 min, and then flow was stopped for 30 min to allow for sufficient time for fibrin digestion by the plasmin. Finally, the remaining plasmin solution was perfused through the channel at the same shear rate. The digested fibrin samples were collected and snap frozen at −70° C. until assayed for D-dimer.

Scanning Electron Microscopy

After plasma perfusion and the heparin wash buffer wash, the glass slide with the fibrin deposit was immersed in a glass slide holder containing 2.5% glutaraldehyde solution for 5 minutes, then immersed in another glass slide holder containing de-ionized water for an additional 5 minutes. The slide was then rinsed in graded ethanol solutions (50%, 70%, 80%, 100% and 100%) for 5 min, and dehydrated once in 50%, and twice in 100% hexamethylsilazane for 5 min. Next, a 10-20 nm layer of gold was sputtered on the dehydrated fibrin deposits. Images were taken with JOEL 7000 field emission SEM (Hitachi, Tokyo, Japan) at an accelerating voltage of 1.5 kV and a working distance of 6 mm. The diameters of 20-30 fibrin fibers were measured with Image J software, averaged and reported with standard deviations.

All of the documents cited herein are incorporated herein by reference.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention. The embodiments described hereinabove are further intended to explain the best mode known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed:

1. A microfluidic device, comprising:
   a first end and a second end;
   a top surface and a bottom surface;
   at least one microfluidic channel having an upper surface and a lower surface enclosed between the top surface and the bottom surface of the microfluidic device, and extending from said first end of the microfluidic device to said second end of the microfluidic device, wherein the at least one microfluidic channel connects a first opening at said first end of the microfluidic device and a second opening at said second end of the microfluidic device, and wherein the first opening, the second opening and the at least one microfluidic channel are in the same plane, and wherein the plane is parallel to the top surface and the bottom surface of the microfluidic device; and
   at least one substrate surface provided in the at least one microfluidic channel, wherein the at least one substrate surface comprises a plurality of lipid coated particles immobilized on the substrate surface, wherein the plurality of lipid coated particles comprises silica, and at least one functional molecule, and wherein the at least one functional molecule induces coagulation, wherein said microfluidic device measures the end products of a coagulation cascade with plasma.

2. The device of claim 1, wherein the substrate surface is functionalized glass.

3. The device of claim 1, wherein the plurality of the lipid coated particles comprises a plurality of particles having a hydrophilic surface.

4. The device of claim 1, wherein the plurality of lipid coated particles comprises one or more phospholipid structures selected from the group consisting of phosphatidylserine, phosphatidylcholine, phosphatidic acid, phosphatidylethanolamine, phosphoinositides, phosphosphingolipids, and combinations thereof.

5. The device of claim 1, wherein the plurality of the lipid coated particles is immobilized to the substrate surface by at least one of bonding selected from the group consisting of an covalent bond, an electrostatic interaction, and hydrogen bond.

6. The device of claim 1, wherein the immobilized plurality of lipid coated particles are in a pattern on the substrate surface to produce an immobilized and patterned lipid coated particles.

7. The device of claim 6, wherein the immobilized and patterned lipid coated particle is integrated into the at least one microfluidic channel.

8. The device of claim 1, further comprising at least one channel to provide a buffer for hydrodynamic focusing.

9. The device of claim 1, wherein the functional molecule is one or more transmembrane proteins.

10. The device of claim 9, wherein the transmembrane protein is selected from the group consisting of tissue factor, thromobomodulin, endothelial cell protein C receptor, glycoprotein IIb/IIIa, glycoprotein VI, glycoprotein Ib/IX/V, P-selectin, glycoprotein IV, CD9, platelet endothelial cell adhesion molecule (PECAM-1), Ras-related protein 1b (rap1b), c-type lectin-like receptor 2 (CLEC-2), intracellular adhesion molecule 1 (ICAM-1), intracellular adhesion molecule 2 (ICAM-2) and combinations thereof.

11. The device of claim 8, wherein the buffer is HEPES buffered saline.

12. The device of claim 1, wherein the at least one surface of the substrate further comprises a monolayer of 3-aminopropyl-trimethoxysilicane.

13. The device of claim 1, wherein a material of the substrate is at least one of glass, plastic, gold, quartz, silicon, silicon nitride, silicon dioxide, polydimethylsiloxane, polystyrene, and polymethyl methacrylate.

14. The device of claim 1, wherein the silica is selected from the group consisting of silica glass and ceramic.

15. The device of claim 1, wherein the silica comprises silica beads.

16. The device of claim 1, wherein the at least one microfluidic channel is capable of receiving fluid at the first end and allowing the fluid to flow through the at least one microfluidic channel.

17. The device of claim 1, wherein the at least one microfluidic channel is split into multiple channels.

18. The device of claim 1, wherein at least one of the at least one substrate surface intersects with at least one of the at least one microfluidic channel.

19. The device of claim 1, wherein the at least one surface of the substrate is hydrophilic.

20. The device of claim 15, wherein the silica beads are hydrophilic.

21. The device of claim 1, wherein the device simulates hemodynamic conditions of a patient.

22. The device of claim 1, wherein the coagulation cascade is measured by thrombin or fibrin generation.

23. The device of claim 1, wherein the plurality of lipid coating particles are immobilized on the substrate surface by a method selected from covalent bonding, electrostatic interactions or hydrogen bonding.

* * * * *